United States Patent
Campbell et al.

(10) Patent No.: US 9,693,862 B2
(45) Date of Patent: Jul. 4, 2017

(54) HOLDERS FOR PROSTHETIC HEART VALVES

(71) Applicant: Edwards Lifesciences Corporation, Irvine, CA (US)

(72) Inventors: Louis A. Campbell, Santa Ana, CA (US); Andrew Phung, Brea, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 858 days.

(21) Appl. No.: 13/948,923

(22) Filed: Jul. 23, 2013

(65) Prior Publication Data

US 2014/0039609 A1    Feb. 6, 2014

Related U.S. Application Data

(60) Provisional application No. 61/677,940, filed on Jul. 31, 2012, provisional application No. 61/779,890, filed on Mar. 13, 2013.

(51) Int. Cl.
*A61F 2/24* (2006.01)
*A61F 2/00* (2006.01)

(52) U.S. Cl.
CPC .......... *A61F 2/2427* (2013.01); *A61F 2/0095* (2013.01); *A61F 2/2412* (2013.01)

(58) Field of Classification Search
CPC .... A61F 2/0095; A61F 2/2427; A61F 2/2433; A61F 2/2436; A61F 2/2439; A61F 2/24;
(Continued)

(56) References Cited

U.S. PATENT DOCUMENTS

| 4,106,129 A | 8/1978 | Carpentier et al. |
| 4,865,600 A | 9/1989 | Carpentier et al. |

(Continued)

FOREIGN PATENT DOCUMENTS

| WO | 9725004 A1 | 7/1997 |
| WO | 0042950 A2 | 7/2000 |

(Continued)

OTHER PUBLICATIONS

International Search Report from Correspinding PCT Application No. PCT/US 2013/052549, Mailed on Nov. 4, 2013.
(Continued)

*Primary Examiner* — Diane Yabut
*Assistant Examiner* — Martin T Ton
(74) *Attorney, Agent, or Firm* — Guy Cumberbatch; Pui Tong Ho

(57) ABSTRACT

An improved holder and storage system for prosthetic heart valves that pre-shields or pre-constricts the commissure posts of the valve to prevent suture looping. Pre-shielding and pre-constriction mean at the time of manufacture, so that the valves are stored with the commissure posts shielded and/or constricted. The holders may have solid legs that directly contact and constrict and hold the commissure posts without the use of sutures in tension that might creep over the time in storage. The holder may have a base in contact with the inflow end and a shaft portion that projects through the valve leaflets and cooperates with movable legs on the outflow end of the valve in contact with the commissure posts. The holders may, alternatively, have flexible leg members that extend through the valve and have distal end portions configured to extend over and shield the tips of commissure posts.

19 Claims, 9 Drawing Sheets

(58) Field of Classification Search
CPC ...... A61F 2/2412; A61F 2/2418; A61F 2/243;
A61F 2/2466; A61F 2/2469
USPC .......................................................... 623/243
See application file for complete search history.

(56) References Cited

U.S. PATENT DOCUMENTS

| | | | |
|---|---|---|---|
| 5,037,434 | A | 8/1991 | Lane |
| 5,403,305 | A | 4/1995 | Sauter et al. |
| 5,476,510 | A | 12/1995 | Eberhardt et al. |
| 5,560,487 | A | 10/1996 | Starr |
| 5,716,401 | A | 2/1998 | Eberhardt et al. |
| 5,720,391 | A * | 2/1998 | Dohm ................ A61F 2/0095 206/363 |
| 5,984,959 | A * | 11/1999 | Robertson ............ A61F 2/2427 623/2.11 |
| 6,090,138 | A | 7/2000 | Chasak et al. |
| 6,126,006 | A | 10/2000 | Addy et al. |
| 6,231,601 | B1 | 5/2001 | Myers et al. |
| 6,409,758 | B2 | 6/2002 | Stobie et al. |
| 6,702,852 | B2 | 3/2004 | Stobie et al. |
| 6,736,845 | B2 | 5/2004 | Marquez et al. |
| 6,964,682 | B2 | 11/2005 | Nguyen-Thien-Nhon et al. |
| 6,966,925 | B2 | 11/2005 | Stobie |
| 7,018,407 | B1 | 3/2006 | Wright et al. |
| 7,033,390 | B2 | 4/2006 | Johnson et al. |
| 7,189,258 | B2 | 3/2007 | Johnson et al. |
| 7,468,073 | B2 | 12/2008 | Johnson et al. |
| 7,503,929 | B2 | 3/2009 | Johnson et al. |
| 7,658,763 | B2 | 2/2010 | Stobie |
| 7,806,926 | B2 * | 10/2010 | Stobie ................... A61F 2/2427 623/2.11 |
| 7,819,915 | B2 | 10/2010 | Stobie et al. |
| 7,871,432 | B2 | 1/2011 | Bergin |
| RE42,395 | E | 5/2011 | Wright et al. |
| 2004/0024451 | A1 | 2/2004 | Johnson et al. |
| 2004/0059413 | A1 | 3/2004 | Argento |
| 2004/0148017 | A1 | 7/2004 | Stobie |
| 2005/0251252 | A1 | 11/2005 | Stobie |
| 2007/0156234 | A1 | 7/2007 | Adzich et al. |
| 2007/0244551 | A1 | 10/2007 | Stobie |
| 2009/0259305 | A1 | 10/2009 | Lane et al. |
| 2010/0004739 | A1 | 1/2010 | Vesely |
| 2010/0249894 | A1 | 9/2010 | Oba et al. |
| 2010/0331972 | A1 | 12/2010 | Pintor et al. |
| 2012/0136434 | A1 | 5/2012 | Carpentier et al. |
| 2012/0150288 | A1 | 6/2012 | Hodshon et al. |

FOREIGN PATENT DOCUMENTS

| | | |
|---|---|---|
| WO | 2004026173 A2 | 4/2004 |
| WO | 2011047137 A1 | 4/2011 |

OTHER PUBLICATIONS

Edwards Lifesciences, "Holder Valve Peri," Sep. 15, 2005; 1 drawing page.
Edwards Lifesciences, "Introducing the New Carpentier Edwards Perimount Magna Aortic Valve Holder," 2005; 2 pages.
International Search Report from corresponding International Application No. PCT/ US2011/062637 dated Nov. 30, 2011.
Medtronic, "Advanced Implant System," 2003; 2 pages.
Medtronic, "The Cinch Advanced Implant System Technology Made Easy," 2003; 2 pages.
Sorin Group Canada Inc. Mitroflow Division, "Aortic Pericardial Heart Valve Instructions for Use," 2004; 2 pages.
St. Jude Medical, "Experience Ease of Implant with Just One Touch," 2005; 4 pages.
St. Jude Medical, "Physician's Manual SJM Biocor Valve," Aug. 6, 2006; 5 pages.

* cited by examiner

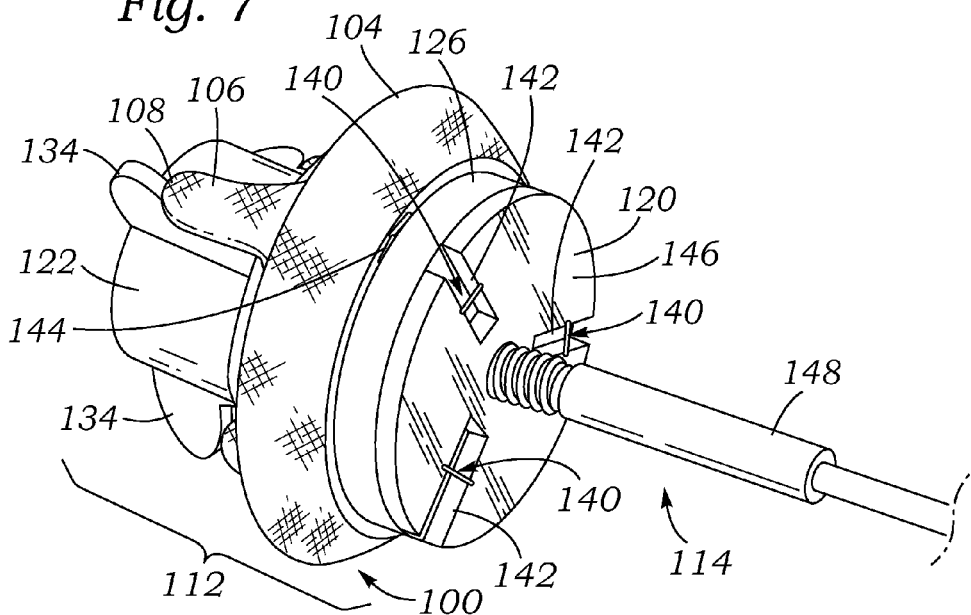
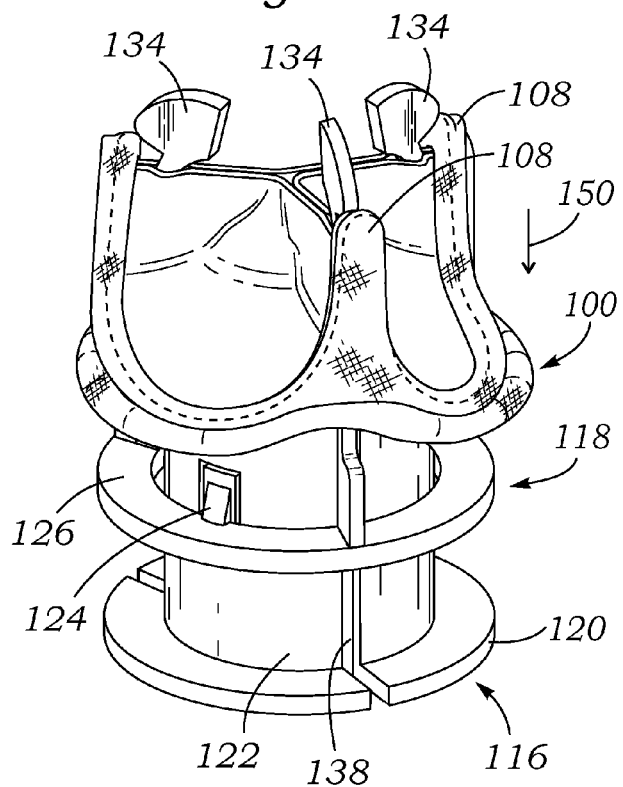

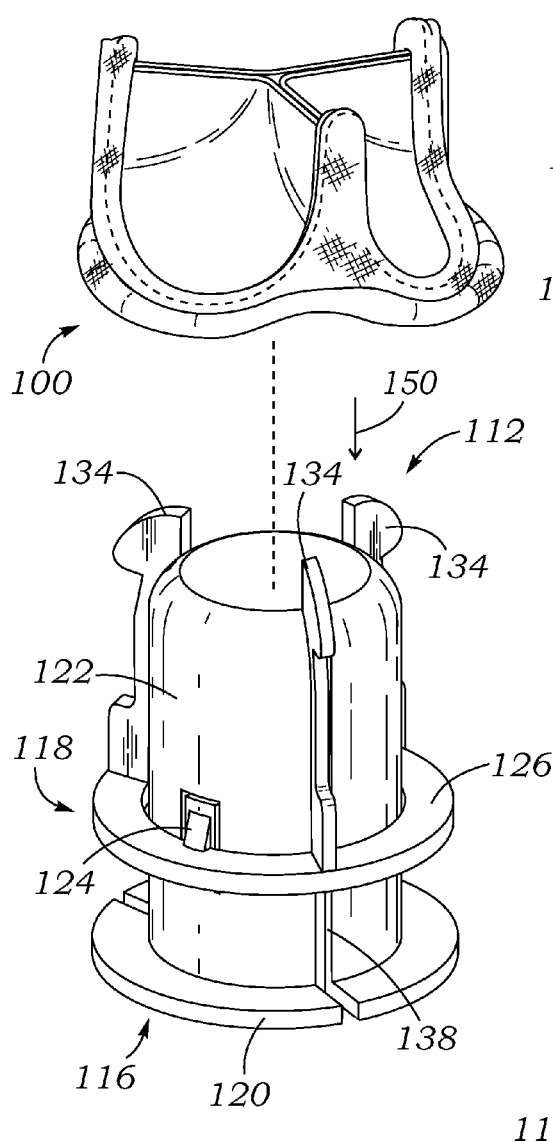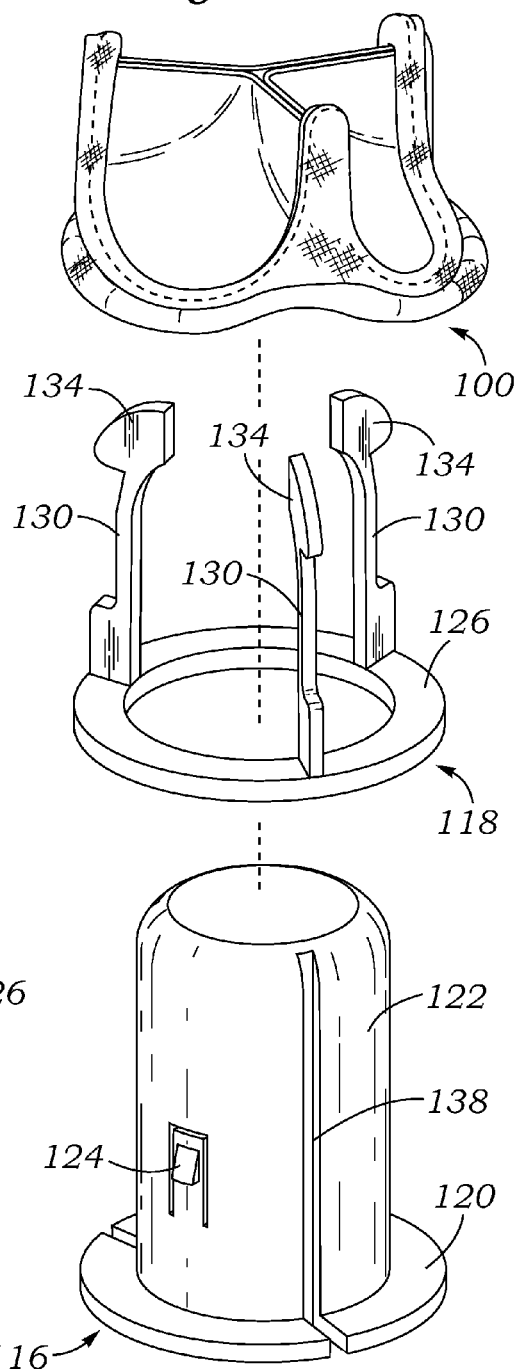

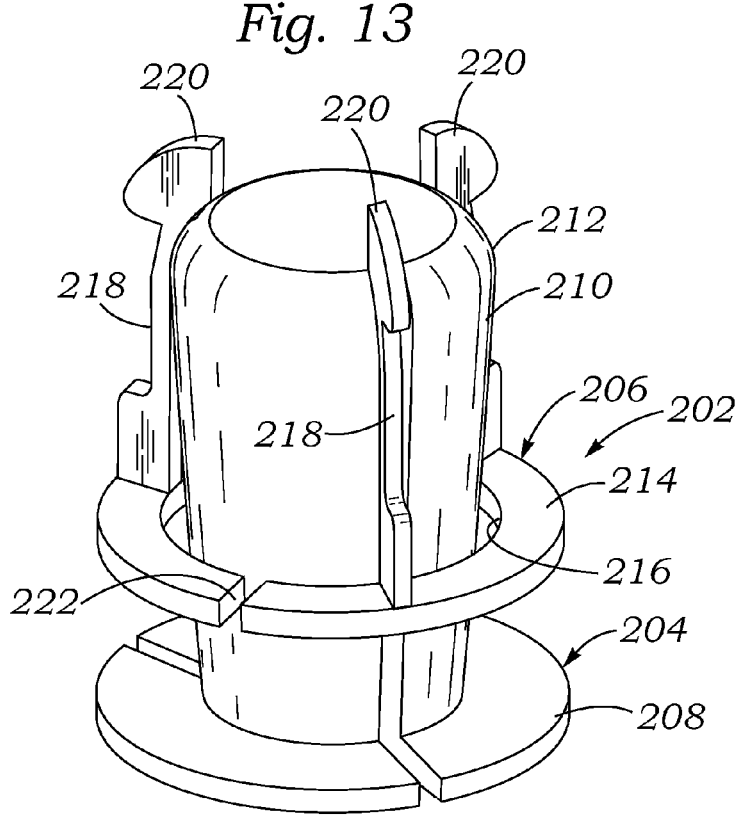
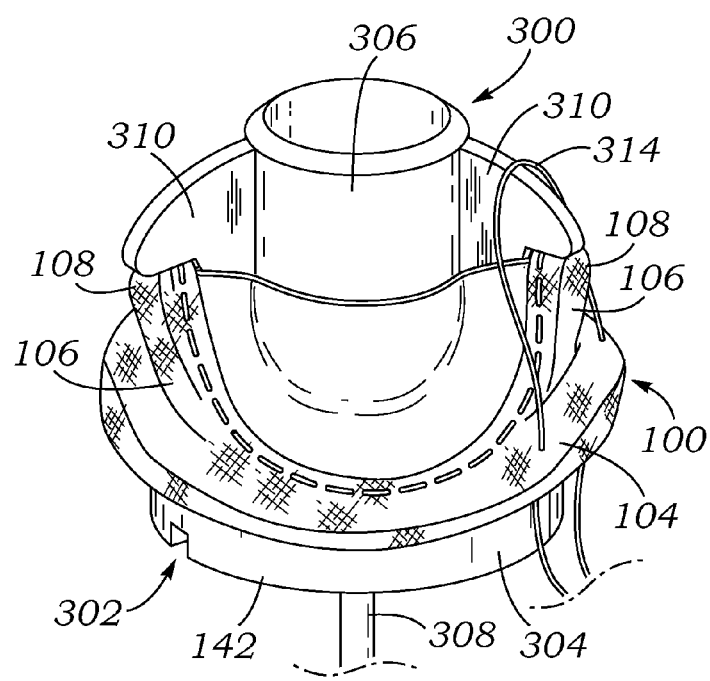

HOLDERS FOR PROSTHETIC HEART VALVES

RELATED APPLICATIONS

The present application claims priority under 35 U.S.C. §119(e) to U.S. Provisional Application Ser. No. 61/677,940 filed on Jul. 31, 2012, and to U.S. Provisional Application Ser. No. 61/779,890 filed on Mar. 13, 2013.

FIELD

The present invention relates to holders and methods of holding and storing that facilitate implantation of prosthetic heart valves by pre-shielding and/or pre-constricting the valve commissure posts.

BACKGROUND

Heart valve disease is a significant cause of morbidity and mortality, resulting from a number of ailments including rheumatic fever and birth defects. The natural heart valves are identified as the aortic, mitral (or bicuspid), tricuspid and pulmonary valves, and each has leaflets to control the directional flow of blood through the heart. Worldwide, approximately 300,000 heart valve replacement surgeries are performed annually, and about one-half of these patients receive bioprosthetic heart valve replacements, which utilize biologically derived tissues for flexible fluid-occluding leaflets.

Heart valve prostheses are either of the mechanical type that originally used a ball and cage and more recently a pivoting mechanical closure, or a tissue type or "bioprosthetic" valve typically constructed with natural-tissue valve leaflets. The most successful bioprosthetic materials for flexible leaflets are whole porcine valves and separate leaflets made from bovine pericardium stitched together to form a tri-leaflet valve. However, flexible leaflets formed of polymeric, fiber-reinforced, and other synthetic materials have also been proposed. The most common flexible leaflet valve construction includes three leaflets mounted to a peripheral support structure and commissure posts that project in a downstream or outflow direction. The leaflets have free edges between the commissure posts that meet or coapt in the middle of the flowstream to permit one-way flow. A suture-permeable sewing ring around the inflow end typically provides a platform for anchoring sutures.

Prosthetic valves typically have a delivery holder centrally located and sutured thereto, and an elongated delivery handle coupled to the holder for manipulating the valve assembly during implant. For the standard delivery approaches, the holder is attached to the inflow side such as the sewing ring for mitral valves and to the outflow side such as the stent cusps or outflow commissure tips for aortic valves.

When placing a flexible leaflet prosthetic valve in the mitral or tricuspid position, the commissure posts are on the leading or blind side of the valve during delivery and implant, and the surgeon uses the holder and an attached handle to slide (parachute) the valve down an array of sutures that have been pre-installed around the mitral annulus and then passed through the valve sewing ring. The mitral position is such that the outflow end with commissure posts is the leading end as it advances toward the left ventricle during implantation, and thus the holder is attached to the inflow (i.e., trailing) end of the valve. The difficulty of the delivery task is compounded by the small access pathway into the left atrium. Suture looping sometimes occurs when one or more of the sutures in the parachute array inadvertently wraps around the inside of one or more of the commissure post tips. If this occurs, the looped suture(s) may slow down the implant procedure, damage one of the tissue leaflets when tightly tied down, or interfere with valve operation and prevent maximum coaptation of the valve leaflets, resulting in a deficiency in the prosthetic mitral valve. These issued can be resolved inter-operatively if the surgeon is aware of the suture looping, but because the loops occur on the blind side of a mitral or tricuspid valve the surgeon might not be aware of a suture loop. If the surgeon does not eliminate the suture loop and leaves a valve implanted with a suture looped over the leaflet it is very likely to result in leaflet tearing forcing what can be an emergency surgery. If after tearing initiates, it is not correctly diagnosed and treated the consequences can be fatal for the valve recipient.

Existing mitral valve holders on the market attempt to mitigate the potential for suture looping of the commissure posts during implantation by moving the posts toward the central axis of the valve (post constriction). For example, U.S. Pat. No. 4,865,600 to Carpentier, et al., provides a holder having a mechanism that constricts the commissure posts inwardly just prior to implantation. The Carpentier device provides an elongate handle to both hold the valve/valve holder combination during implantation, as well as to cause the commissure posts to constrict inwardly. More recently, U.S. Pat. Nos. 6,409,758, 6,702,852, 6,964,682, 6,966,925, and 7,033,390 disclose heart valve holder systems that resist suture looping.

Bioprosthetic heart valves configured for implanting in the aortic or pulmonic position also can benefit from constriction of the commissure posts. That is, although the holder attaches to the outflow side of the valve, the lower radial profile of the commissure posts eases implantation, such as through an aortotomy.

Bioprosthetic heart valves are conventionally packaged in jars filled with preserving solution for shipping and storage prior to use in the operating theater. Glutaraldehyde is widely used as a storage solution due to its sterilant properties. Because glutaraldehyde is a fixative, or cross-linking agent, and the fixing process is ongoing, bioprosthetic valves are stored in the jars with their leaflets in the closed or coapting position and the commissure posts relaxed, not constricted. This is to ensure that the leaflets fix in the shape they are supposed to have when closed. Otherwise the leaflets may assume a distorted shape which could detrimentally affect functioning, such as regurgitation upon implant. As a consequence, prior art devices that constrict the commissures are actuated in the operating room, just prior to implant of the valve. Various designs are available, each of which require an affirmative action which creates a risk that the operating room staff will not completely constrict the commissure posts, possibly leading to suture looping. To compound the problem, the devices sometimes require several precise steps, which can be confusing in the pressured environment of a heart surgery with the patient on bypass.

Despite a number of advances, there is still a need in the art for a holder and associated packaging for tissue-type prosthetic mitral valves that helps prevent suture looping and is more intuitive to use.

SUMMARY

The present application provides a holder and associated packaging system for prosthetic heart valves that is more intuitive to use and pre-constricts and/or pre-shields the commissure posts of the valve to prevent suture looping and ease implantation. Pre-constriction and pre-shielding mean at the time of manufacture, so that the valves are stored for at least 24 hours with the commissure posts constricted and/or shielded. The valve may be bioprosthetic and stored dry to avoid continued cross-linking of the leaflets. Capping the glutaraldehyde terminates the cross-linking process by consuming all of the amines eliminating cross-linking sites for the aldehydes. In certain embodiments, the holders have solid legs that directly contact, constrict and hold the commissure posts without the use of sutures in tension that might creep over the time in storage.

For an aortic valve, the holder may have a solid hub and legs on the outflow end of the valve that retain the commissure posts inward. For a mitral valve, the holder may have a base in contact with the inflow end and a shaft portion that projects through the valve leaflets and cooperates with movable legs on the outflow end of the valve in contact with the commissure posts. Disclosed methods include constricting the valve commissure posts and then packaging the valve in a sterile container.

The present application also describes embodiments a valve holder for a prosthetic heart valve that shields the tips of the commissure posts during implantation of the prosthetic heart valve at a native heart valve annulus to prevent suture looping and ease implantation without necessarily pulling or otherwise constricting the commissure posts radially inward. The holder can have a base in contact with an inflow end of a prosthetic valve and a shaft portion that projects through the valve leaflets and cooperates with flexible members on an outflow end of the prosthetic valve to shield the tips of commissure posts. Disclosed methods include shielding the valve commissure posts and then packaging the valve in a sterile container along with the valve holder.

In one representative embodiment, a valve holder for a prosthetic heart valve comprises a plurality of angularly spaced, leg members configured to extend at least partially through the prosthetic valve in the outflow direction. The leg members have distal end shielding portions and are moveable between a radially outward position and a radially inward position, wherein when the leg members are in the radially outward position, the distal end portions extend over and shield the tips of the commissure posts of the prosthetic valve and wherein when the leg members are in the radially inward position, the distal end portions are spaced radially inward of the commissure tips and can be withdrawn through the prosthetic valve in a direction toward the inflow end.

In another representative embodiment, a prosthetic heart valve assembly comprises a prosthetic heart valve and a valve holder. The prosthetic heart valve has an inflow end, an outflow end, and plural commissure posts ending in tips projecting in an outflow direction. The valve holder comprises an inner body member and an outer shielding member. The outer shielding member comprises a plurality of angularly spaced, flexible leg members, each having a proximal portion extending through the prosthetic valve and a distal end portion disposed over a tip of a corresponding commissure post. The inner body member comprises a shaft extending through the leg members and retaining the leg members in a radially outward position in which the distal end portions cover the tips of the commissure posts. Removal of the shaft from the leg members in a direction toward the inflow end of the prosthetic valve the allows the leg members to flex to a radially inward position away from the tips of the commissure posts to allow the leg members to be withdrawn through the prosthetic valve in a direction toward the inflow end.

In another representative embodiment, a method of implanting a prosthetic heart valve comprises providing a prosthetic heart valve assembly comprising a prosthetic heart valve and a valve holder. The prosthetic valve has an inflow end, an outflow end, and plural commissure posts ending in tips projecting in an outflow direction. The valve holder comprises an inner body member and an outer shielding member. The outer shielding member comprises a plurality of angularly spaced, flexible leg members, each having a proximal portion extending through the prosthetic valve and a distal end portion disposed over a tip of a corresponding commissure post. The inner body member comprises a shaft extending through the leg members and retaining the leg members in a radially outward position in which the distal end portions cover the tips of the commissure posts. The method further comprises delivering and securing the prosthetic valve to a native valve annulus in the heart, retracting the inner body member through the inflow end of the prosthetic valve, causing the leg members to flex radially inwardly away from the commissure posts, and then retracting the shielding member through the inflow end of the prosthetic valve.

In another representative embodiment, a method of packaging a prosthetic heart valve comprises providing a prosthetic heart valve having an inflow end, an outflow end, and plural commissure posts ending in tips projecting in an outflow direction, and providing a shielding member comprising a plurality of flexible leg members, each having a distal end portion. The leg members are inserted into the inflow end of the prosthetic valve until the distal end portions are distal to the tips of the commissure posts and the leg members are then bent or deflected radially outward such that the distal end portions cover the tips of the commissure posts. The prosthetic heart valve and the shielding member can then be packaged for storage and/or shipping.

BRIEF DESCRIPTION OF THE DRAWINGS

Features and advantages of the present invention will become appreciated as the same become better understood with reference to the specification, claims, and appended drawings.

FIG. 7 is a side perspective view of the exemplary assembled pre-shielded prosthetic heart valve assembly of FIG. 6 with a main shaft of a delivery tool attached to an inflow end of a valve holder.

FIG. 8 is a perspective view of the exemplary pre-shielded prosthetic heart valve assembly of FIG. 6 in a partially dis-assembled state in which the distal end portions are in a radially inward position and an inner shaft is partially retracted such that a tab on an inner shaft contacts a base ring of the shielding member.

FIG. 9 is a perspective view of the exemplary pre-shielded prosthetic heart valve assembly of FIG. 6 shown in a dis-assembled state apart from the prosthetic valve.

FIG. 10 is an exploded, perspective view of the exemplary pre-shielded prosthetic heart valve assembly of FIG. 6.

FIG. 13 is side perspective view of the valve holder of the assembly shown in FIG. 12.

FIG. 14 is a perspective view of another embodiment of a pre-shielded prosthetic heart valve assembly in an assembled state showing an implantation suture contacting the shielding portion of the assembly.

DETAILED DESCRIPTION

Figure 1A:
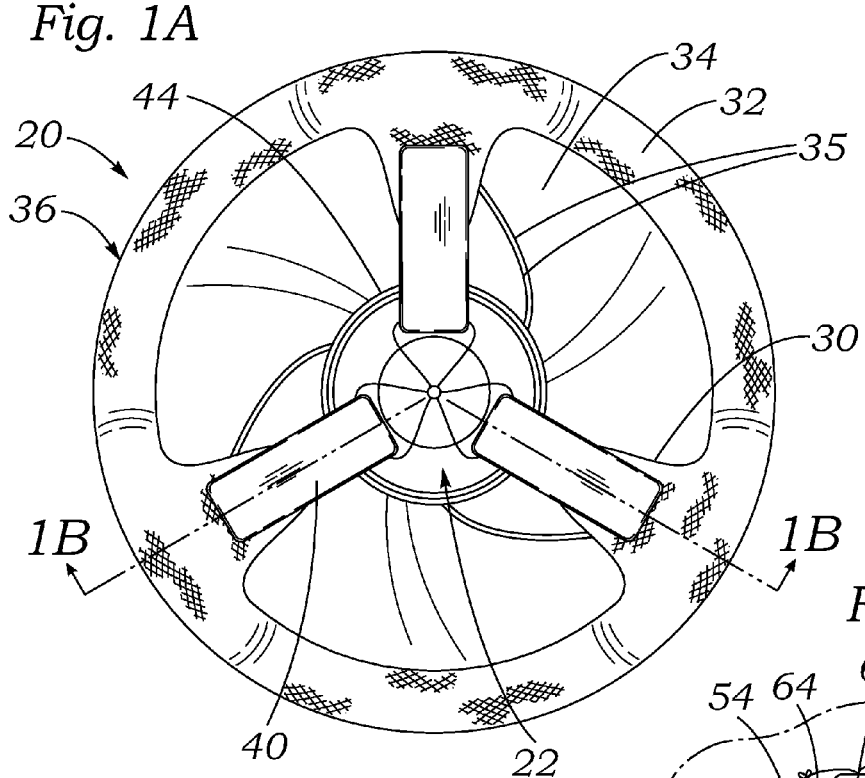
FIG. 1A is a top plan view of a prosthetic heart valve from an outflow end showing portions of an exemplary assembled valve holder of the present application secured thereto.

The present invention provides improved systems and methods for packaging, storing and delivering prosthetic heart valves to reduce complications during valve delivery. The prosthetic heart valves can include flexible, typically bioprosthetic, leaflets that coapt in the flowstream and are supported by a surrounding stent structure including upstanding commissure posts. As is well known in the art, the peripheral edges of the leaflets, either separate or within a whole xenograft valve, are secured to the surrounding stent structure including the upstanding commissure posts which are cantilevered in the outflow direction. The commissure posts are capable of flexing to a certain degree to accommodate the forces of fluid dynamics after implant. The flexing of the commissure posts helps the flexible leaflets both close and open at the appropriate time, and mimics the action of the natural commissures of the respective heart valve annulus. However, because the commissure posts extend axially in the outflow direction, they present problems during delivery of the valve to the target implantation site.

The present application describes systems and methods for pre-constricting the upstanding commissure posts so that they flex radially inward and present a smaller radial profile during delivery of the valve by the surgeon to the target implantation site. The present application also describes systems and methods for pre-shielding the tips of the upstanding commissure posts during delivery without necessarily constricting the commissure posts. The prosthetic heart valve assembly can include a holder and a plurality of flexible members extending through the prosthetic valve and having distal end portions extending over and shielding the tips of the commissure posts. The terms "pre-constricting" and "pre-constricted" refer to constriction of the commissure posts prior to the operating room technicians opening the sterile packaging. Likewise, the terms "pre-shielding" and "pre-shielded" refer to shielding of the tips of the commissure posts prior to the operating room technicians opening the sterile packaging. In other words, the prosthetic heart valve and a holder that pre-constricts and/or pre-shields the commissure posts emerges assembled from the packaging, substantially ready for connection to a delivery handle and delivery (after washing off any preserving solution if necessary).

The present application is useful for prosthetic heart valves having commissure posts for any implant site, but is particularly useful for mitral and aortic valves. Furthermore, the present application describes techniques that are particularly useful with dry prosthetic tissue heart valves that do not require liquid containment during storage. However, it is conceivable that the present application could be applicable to "wet" prosthetic heart valves if precautions are taken so that long-term storage of the valves with the commissure posts constricted does not result in distorted leaflets. For example, it is conceivable that synthetic leaflets may someday be successfully used which are not fixed, or cross-linked, and therefore might be stored wet. Alternatively, bioprosthetic leaflets that are fully fixed and are not affected by long-term storage with the commissure posts constricted might benefit from the principles discussed here. In short, the type of prosthetic heart valve or leaflets should not be considered limited unless explicitly stated by an applicable claim.

Figure 1C:
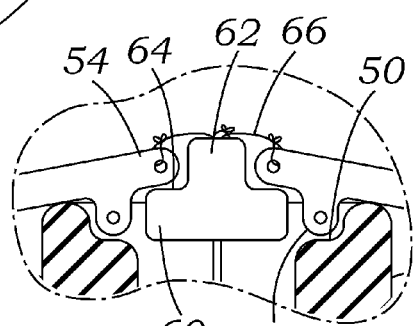
FIG. 1C is an enlarged view taken from FIG. 1B showing an upper end of the valve holder.
Figure 1B:
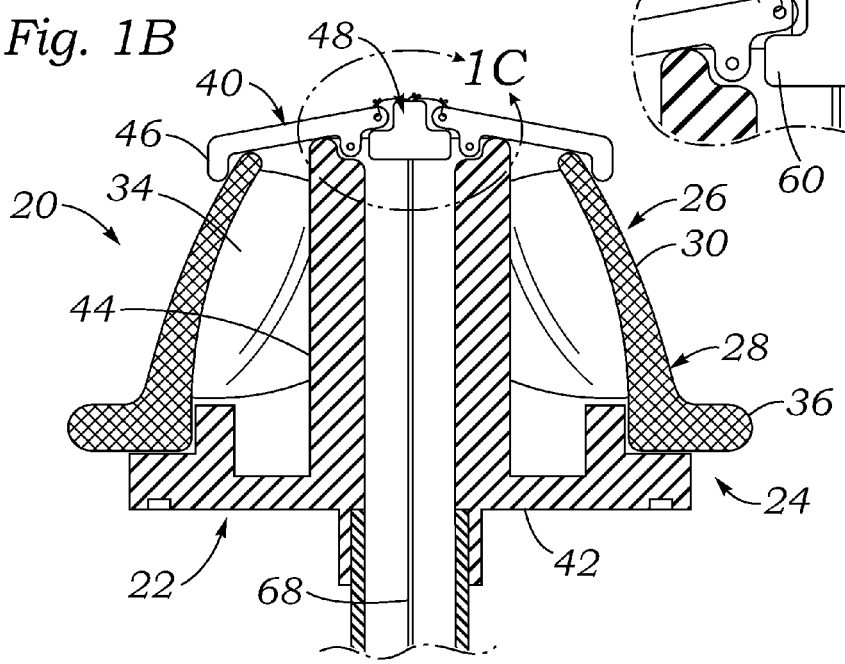
FIG. 1B is a sectional view taken along line 1B-1B in FIG. 1A illustrating the valve holder extending through the heart valve and having movable legs that constrict commissure posts of the heart valve radially inward.

Now with reference to FIGS. 1A and 1B, a prosthetic heart valve 20 is shown assembled to a valve holder 22 of the present application. The heart valve 20 includes an inlet end 24 and an outlet end 26 separated along a vertical flow axis through the middle of the valve. A cloth-covered frame assembly or support frame 28 defines a periphery and flow orifice of the valve and includes commissure posts 30 that project generally axially in the outflow direction separated by arcuate cusps 32 that curve in the inflow direction. Three flexible leaflets 34 couple to the frame 28 and extend inward therefrom. The leaflets 34 attach along an undulating line that follows the commissure posts 30 and cusps 32. A suture-permeable sewing ring 36 surrounds the inflow end of the valve 20, and may have a planar peripheral shape as shown or a shape which undulates upward a short distance in the vicinity of the three commissure posts 30.

It should be understood that the terms inflow/inlet and outflow/outlet refer to the direction of blood flow through the valve 20, which is upward in the orientation shown. Additionally, because the illustrated valve 20 is for implanting at the mitral annulus, the outlet end 26 with the projecting commissure posts 30 forms the leading or distal end of the valve during delivery, while the inlet end 24 is the trailing or proximal end. Thus, at least in the context of the heart valve 20 and holder 22 assembly of FIGS. 1-2, with regard to directions the terms inlet and proximal are synonymous, as are the terms outlet and distal.

As mentioned above, the prosthetic heart valve 20 and other prosthetic heart valves described herein may comprise a number of existing heart valves which have commissure posts 28, and the particular construction of the heart valve aside from having commissure posts is not considered to be an essential part of the present application. However, as will be explained, bioprosthetic heart valves that are stored dry are particularly suitable for integration with the disclosed holders and techniques.

Techniques are known for drying and storing bioprosthetic heart valves without immersing them in a preservative solution. The term "dried" or "dry" bioprosthetic heart valves refers simply to the ability to store those heart valves without the preservative solutions, and the term "dry" should not be considered synonymous with brittle or rigid. Indeed, "dry" bioprosthetic heart valve leaflets may be relatively supple even prior to implant. There are a number of proposed methods for drying bioprosthetic heart valves, and for drying tissue implants in general, and the present application contemplates the use of valves processed by any of these methods. A particularly preferred method of drying bioprosthetic heart valves is disclosed in U.S. Patent Publication No. 2008/0102439 to Tian, et al. An alternative drying method is disclosed in U.S. Pat. No. 6,534,004 to Chen, et al. Again, these and other methods for drying bioprosthetic heart valves may be used prior to implementing the storage techniques described herein.

One such strategy is to dehydrate the bioprosthetic tissue in a glycerol/ethanol mixture, sterilize with ethylene oxide, and package the final product "dry." This process eliminates the potential toxicity and calcification effects of glutaraldehyde as a sterilant and storage solution. There have been several methods proposed to use sugar alcohols (i.e., glycerine), alcohols, and combinations thereof as post-glutaraldehyde processing methods so that the resulting tissue is in a "dry" state rather than a wet state with excess glutaraldehyde. Glycerol-based methods can be used for such storage, such as described in Parker et al. (Thorax 1978 33:638). Likewise, U.S. Pat. No. 6,534,004 (Chen et al.) describes the storage of bioprosthetic tissue in polyhydric alcohols such as glycerol. In processes where the tissue is dehydrated in an ethanol/glycerol solution, the tissue may be sterilized by ethylene oxide (ETO), gamma irradiation, or electron beam irradiation.

More recently, Dove, et al. in U.S. Patent Publication No. 2009/0164005 propose solutions for certain detrimental changes within dehydrated tissue that can occur as a result of oxidation. Dove, et al. propose permanent capping of the aldehyde groups in the tissue (reductive amination). Dove, et al. also describe the addition of chemicals (e.g. antioxidants) to the dehydration solution (e.g., ethanol/glycerol) to prevent oxidation of the tissue during sterilization (ethylene oxide, gamma irradiation, electron beam irradiation, etc.) and storage. Tissue processed in accordance with the principles disclosed in Dove, et al. will be termed, "capped tissue," and therefore heart valves which use such tissue will be termed, "capped tissue valves." Capping the glutaraldehyde terminates the cross-linking process by consuming all of the amines eliminating cross-linking sites for the aldehydes, and it is believed that this in conjunction with removing the tissue valve out of the cross-linking solution (e.g., glutaraldehyde) by storing dry is the most effective way to terminate the cross-linking process.

As seen in FIG. 1B, the valve holder 22 extends through the heart valve 20 and has movable legs 40 that constrict the commissure posts 30 of the heart valve radially inward. More specifically, the valve holder 22 comprises a relatively wide base portion 42 in contact with the inflow end 24 of the heart valve 20, and an axially elongated shaft portion 44 extending in the distal direction from the base portion through the heart valve. The shaft portion 44 projects along the central axis and distally beyond the leaflets 34 of the heart valve. The movable legs 40 are arranged to pivot about a top end of the shaft portion 44, as will be described below. There are three movable legs 40 corresponding to each of the three valve commissure posts 30.

Each of the movable legs 40 has an outer end with a short finger 46 that extends down on the outside of a respective commissure post 30. As seen in FIG. 1C, an inner end of each of the legs 40 has a pivot and a lever structure permitting a locking plug 48 to actuate the leg 40. More specifically, the upper end of the holder shaft portion 44 includes a step 50 formed on an inner wall thereof. A fulcrum projection 52 on each of the movable legs 40 seats on the step 50, while a lever projection 54 extends radially inward therefrom. In the illustrated embodiment, the locking plug 48 includes a larger diameter lower portion 60 and a smaller diameter upper portion 62 that creates a ledge 64 which receives the lever projections 54 of the movable legs 40, as shown in FIG. 1C. Tethers 66 connect the lever projections 54 to an upper end of the locking plug 48. A pull wire 68 attached to the lower end of the locking plug 48 permits the user to displace the locking plug in a proximal direction.

FIGS. 1A and 1B illustrate the assembled prosthetic heart valve 20 and holder 22 as they are provided by the manufacturer in a sterile shipping container or packaging. In this configuration, the valve commissure posts 30 are pulled inward and held by the movable legs 40 of the holder 22. As seen from the outflow end in FIG. 1A, the leaflets 34 curl up somewhat such that their coapting free edges 35 can be seen around the outside of the holder shaft portion 44. After the commissure posts 30 are permitted to flex outward into their functional positions, the leaflet free edges 35 extend generally radially inward from respective commissure posts toward the central axis in a trefoil configuration (not shown). As explained above, the prosthetic heart valve 20 is preferably stored dry with the bioprosthetic tissue used for the leaflets 34 treated to enable storage without a liquid preservative. As such, the leaflets 34 are fully fixed and are not subject to ongoing cross-linking in the preservative solution. Consequently, even though the leaflets 34 are deformed somewhat from their functional shapes during storage, as seen in FIG. 1A, they will resume their proper functional shapes after removal of the holder 22.

It should be understood that the holder 22 with the legs 40 constricting the commissure posts 30 remains in place during delivery of mitral valve 20 until the sewing ring 36 seats at the mitral annulus. Constriction of the commissure posts 30 is only required during delivery down the array of pre-installed anchoring sutures. The extent to which the commissure posts 30 are flexed and held inward from the time of manufacture depends somewhat on the materials used for the cloth-covered support frame 28. That is, the support frame 28 (or components therein) has a material stress limit that determines the maximum inward angle at which the commissure posts 30 can be flexed and held for extended periods of time. Beyond that stress limit, some material including the metals used to construct heart valves would experience plastic or permanent deformation. Polymer materials when stressed above a point that is characteristic of the material and the storage temperature may experience creep leading to permanent deformation and possibly malfunction after implant. In one embodiment, the commissure posts 30 assume a slight inward angle in their relaxed, functional configuration, and are flexed and held inward farther by the holder 20 by an additional 15-30°. For instance, this translates into an additional inward bending distance of between about 4-5 mm for an average size valve, with the absolute distance being somewhat smaller for smaller valves and vice-versa. Again, this angular deformation depends on the desired radial delivery profile governed by the material stress limits in the support frame 28.

Figure 2A:
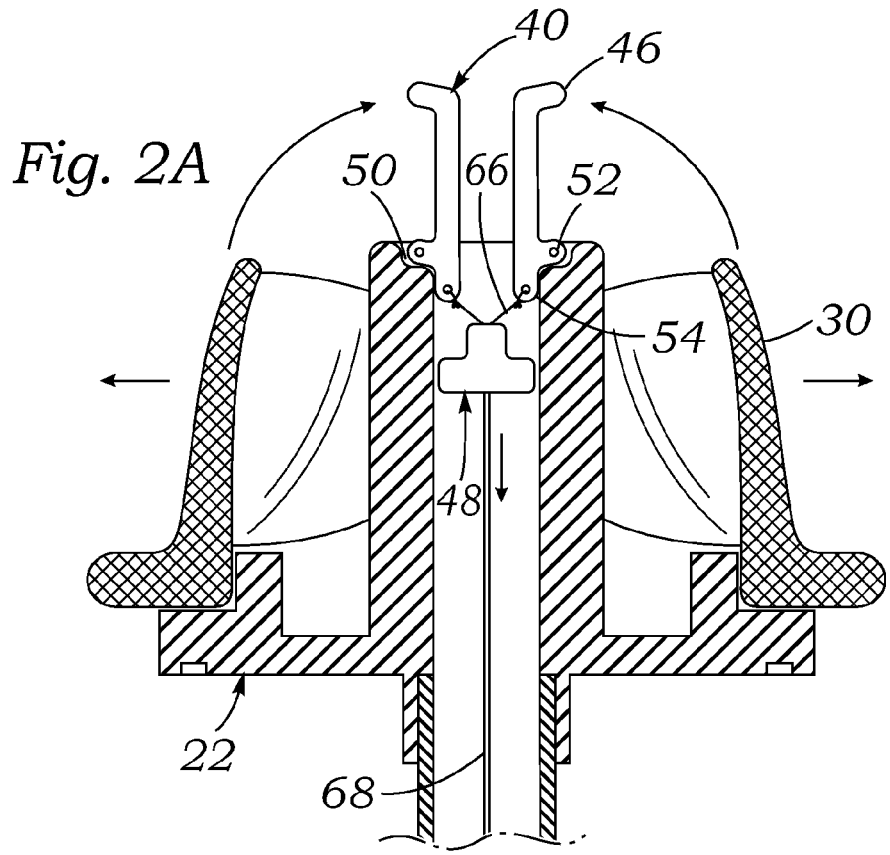
FIGS. 2A-2C are sectional views as in FIG. 1B showing several steps in detachment and removal of the valve holder from the prosthetic heart valve.
Figure 2B:
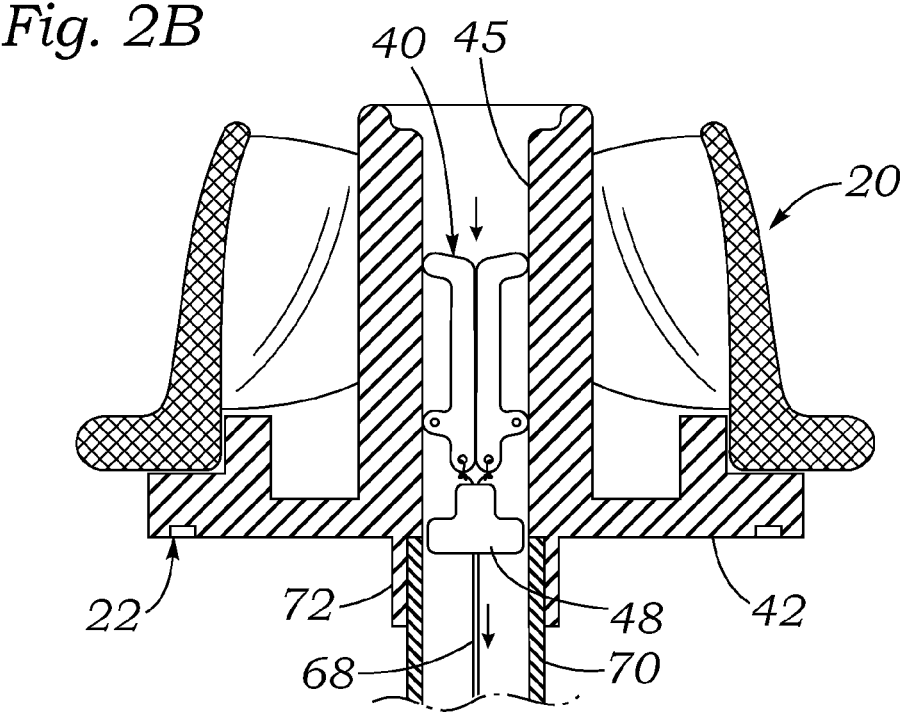
Figure 2C:
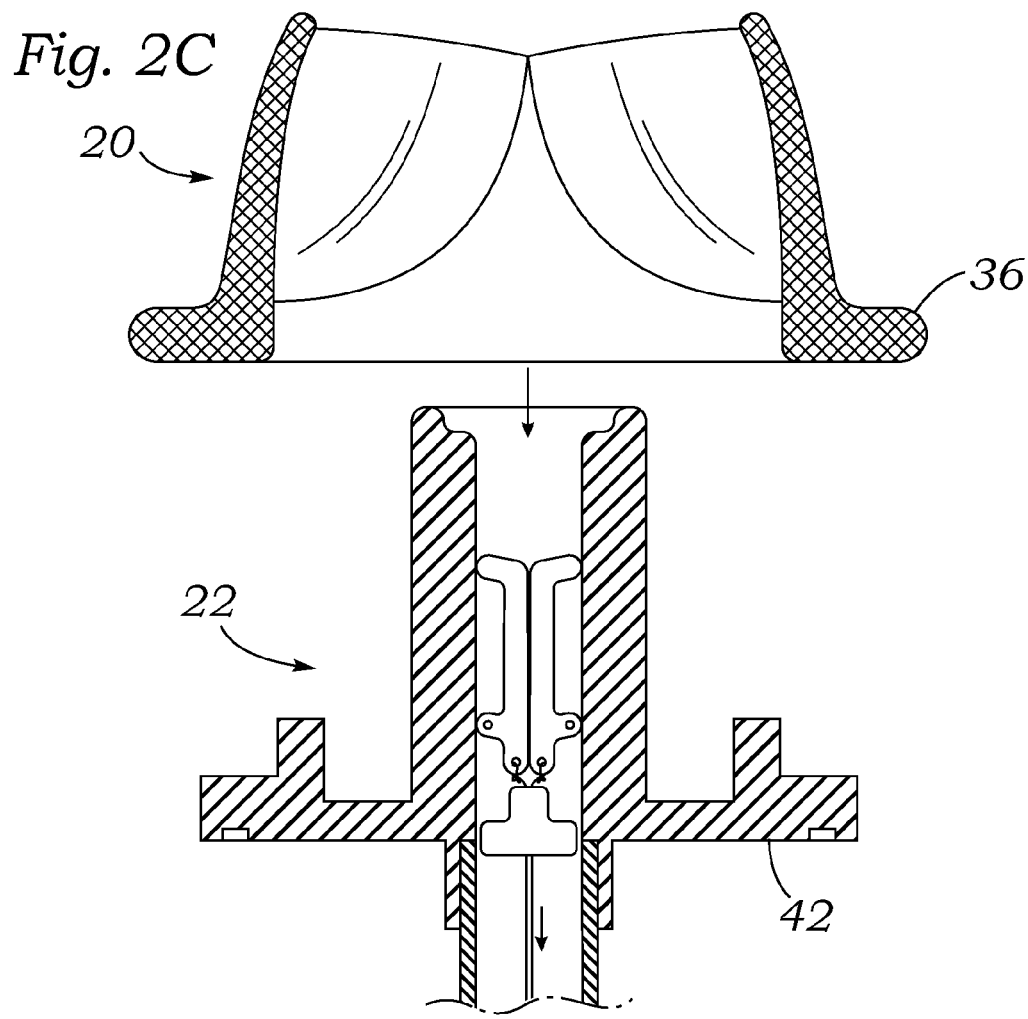

FIGS. 2A-2C are sectional views as in FIG. 1B showing several steps in detachment and removal of the valve holder 22 from the prosthetic heart valve 20, which occurs after seating the heart valve against the target annulus. FIG. 2A shows proximal displacement of the pull wire 68 and locking plug 48. By virtue of the connecting tethers 66, this movement also pulls the lever projections 54 on the movable arms 40 in a proximal direction. The fulcrum projections 52 step 50 on the inside of the holder shaft portion 44, and cause the movable arms 40 to pivot inwards as shown. This releases the fingers 46 of the arms 40 from the respective commissure posts 30, which therefore spring outward into their relaxed, functional positions.

FIG. 2B shows further proximal displacement of the pull wire 68 and locking plug 48, which also pulls the movable arms 40 together and through a lumen 45 of the holder shaft portion 44. The moving parts of the holder 22 can therefore be removed completely from the implantation site, possibly through a tubular handle 70. The handle 70 connects to a proximal sleeve 72 on the holder 22, and may be flexible to enable passage through non-linear access channels.

Finally, FIG. 2C illustrates removal of the entire holder 22 from the prosthetic heart valve 20. In a preferred embodiment, no sutures are used to connect the holder 22 to the valve 20, the latter simply being held between the arms 40 and the base portion 42 of the holder, as in FIG. 1B. Alternatively, although not shown, connecting sutures may be placed through the outer peripheral edge of the base portion 42 and through the valve sewing ring 36. By attaching both ends of each connecting suture to the holder 22, and providing a cut point or well where the suture can be severed in the middle, each of the connecting sutures can be removed with the holder by simply severing the connecting sutures.

Figure 3A:
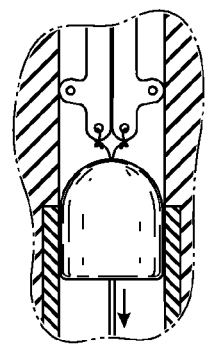
FIGS. 3A and 3B illustrate alternative locking plugs for use in the exemplary heart valve holder of the present application.
Figure 3B:
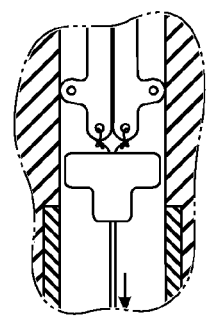

FIGS. 3A and 3B illustrate alternative locking plugs for use in the exemplary heart valve holder of the present application.

Figure 4A:
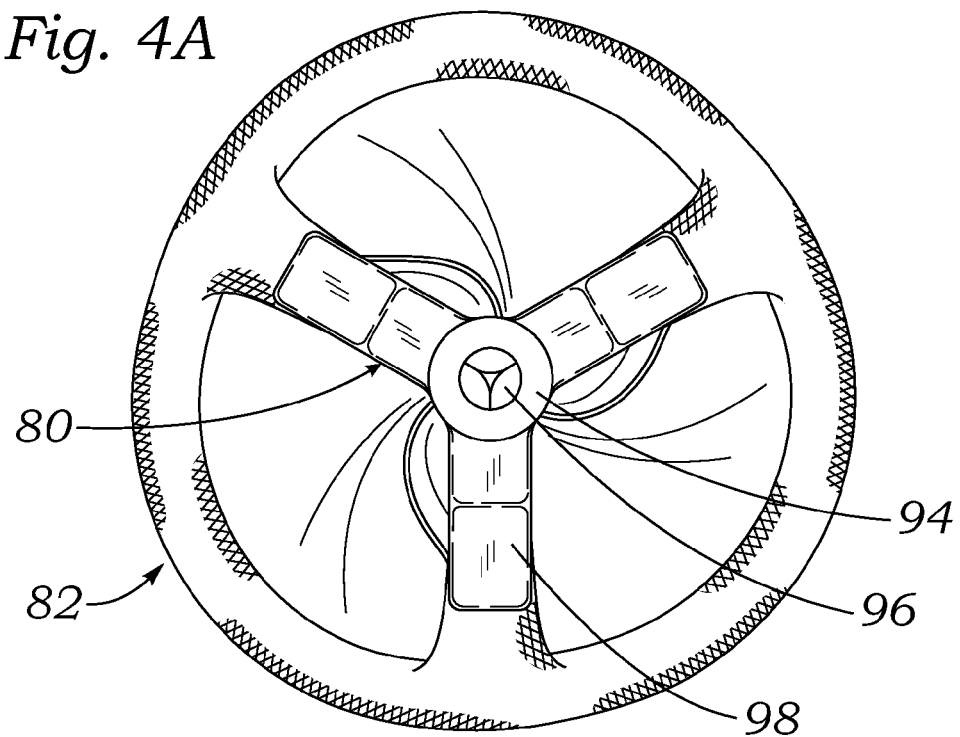
FIGS. 4A and 4B are top plan and side elevational views, respectively, of an alternative constricting-type valve holder of the present application assembled with a prosthetic heart valve, preferably for either aortic or pulmonic implant.
Figure 4B:
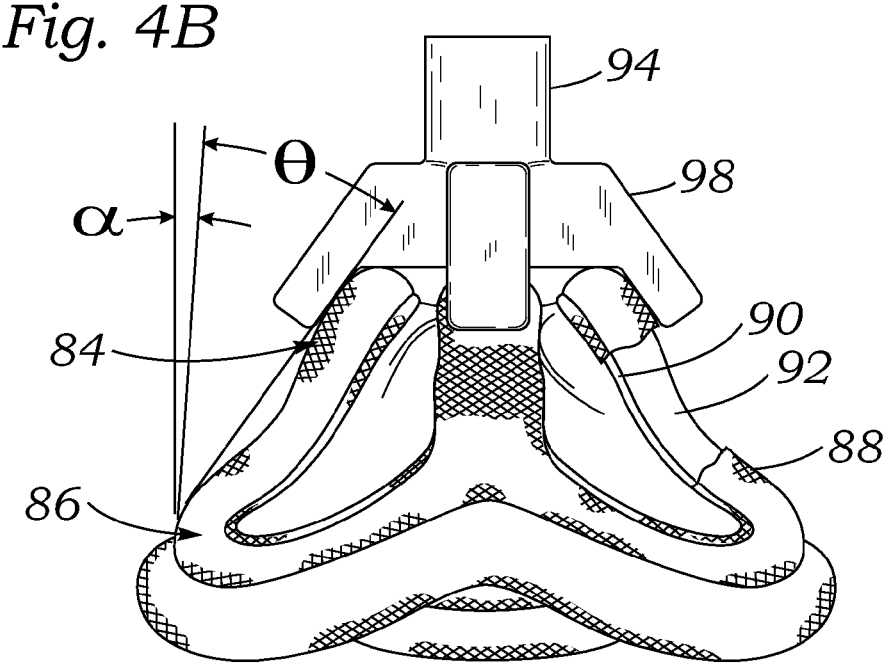

FIGS. 4A and 4B illustrate an alternative pre-constricting valve holder 80 of the present application assembled with a prosthetic aortic heart valve 82. As mentioned above, during delivery of aortic heart valves the inflow end is the leading or distal end, while the outflow end with its commissure posts is the trailing or proximal end. As such, the valve holder 80 couples to the outflow end of the valve 82, or to the tips of the commissure posts 84. As before, the prosthetic valve 82 further includes a support frame that defines three upstanding commissure posts 84 alternating with three arcuate cusps 86. A cloth covering 88 is removed on the right side to expose an exemplary support frame construction. Specifically, the support frame includes a wireform 90, typically metallic, and a stent 92, typically polymeric. Various internal constructions of valve support frames are known in the art, and the illustrated embodiment should not be considered limiting.

The valve holder 80 includes a central hub 94 having a cavity 96 to which a delivery handle (not shown) may be attached. Three legs 98 extend outwardly and down at an angle around the outside of and in direct contact with each of the commissure posts 84, thus maintaining the commissure posts inwardly constricted by an angle θ. The angle θ is taken from the line through the commissure posts 84 in their relaxed, functional configuration, which is slightly offset from the vertical by an angle α of about 5° as shown. In one embodiment, the commissure posts 84 are flexed and held inward by the holder 20 by about 15-30°, which again depends on the desired radial delivery profile governed by the material stress limits in the support frame.

In one embodiment, the legs 98 of the holder 80 are secured to the tips of the commissure posts 84 using sutures or similar expedient which can be easily detached. Alternatively, the legs 98 may have retractable features, such as small barbs, that enable them to hold the tips of the commissure posts 84 during storage and delivery of the valve to the target implantation site, but enable quick release. Still further bands or ties (not shown) around both the commissure posts 84 and legs 98 may be used to hold the components together until time to release the valve.

The holder 80, and in particular the outwardly extending legs 98, should be made of a material that will not creep significantly under constant load at the temperatures at which the valve will be stored. Metallic materials including stainless steel, cobalt chromium (CoCr), or titanium would be preferable, but also some polymers are acceptable if the creep resistance will not cause the commissure posts 84 to move significantly during storage. For instance, some high-temperature polymers like polyetherimide may be suitable. Additionally, polymers may be reinforced with fibers to prevent creep. Alternatively, the holder can be designed with a high area moment of inertia so the strain is minimized to reduce creep. Creep is a function of material, temperature and the level of stress on the material so thick sections opposing the load from the stent posts could reduce the level of strain.

Figure 5:
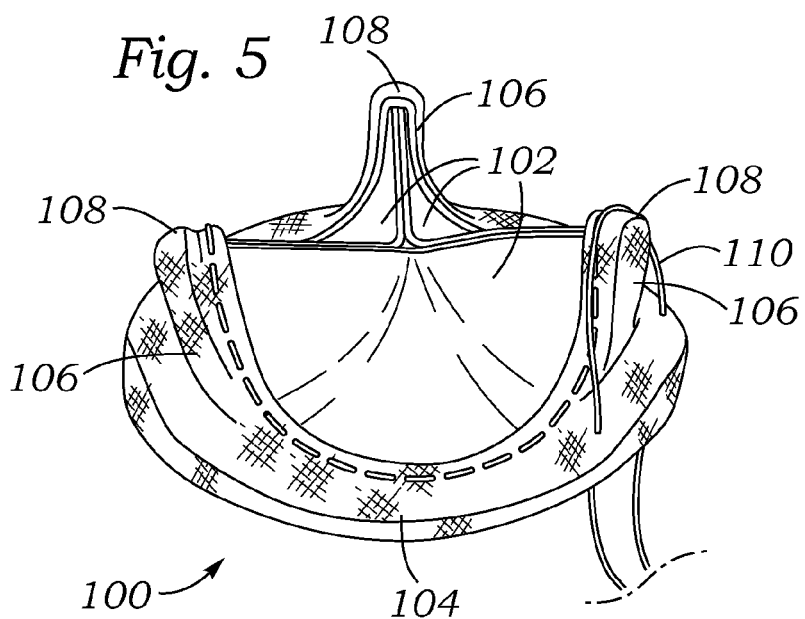
FIG. 5 is a perspective view of a prosthetic heart valve depicting a suture looped around a tip of a commissure post of the prosthetic valve during implantation of the prosthetic valve.

FIG. 5 shows an exemplary prosthetic heart valve 100 and depicts how a suture can become looped on a commissure post of the valve. The prosthetic heart valve 100 comprises an inflow end, an outflow end, leaflets 102, a sewing ring 104 at the inflow end, and three commissure posts 106 projecting in an outflow direction and ending in tips 108. In the absence of shielding of the tips and/or constriction of the posts 106 during delivery of the prosthetic heart valve 100, a suture 110 may become hooked on one or more of the commissure tips 108 of one of the commissure posts 106, as depicted in FIG. 5.

FIGS. 6-10 show a prosthetic heart valve assembly 112 comprising the prosthetic heart valve 100 and a valve holder 114, according to another embodiment. As with the embodiment of FIGS. 1-4, the prosthetic heart valve 100 used in this embodiment and other embodiments described herein can comprise any number of existing prosthetic valves which have commissure posts 106, and the particular construction of the prosthetic valve aside from having commissure posts is not considered to be an essential part of the present application.

The valve holder 114 is configured to shield the commissure post tips 108 to protect against suture looping during delivery of the prosthetic valve to a native valve annulus. In particular embodiments, the valve holder 114 need not constrict the commissure posts 106 and instead shield the commissure post tips during valve delivery while the commissure posts can remain in their non-deflected, functional state. The valve holder 114 in the illustrated embodiment comprises an inner body member 116 and an outer shielding member 118 that is disposed around the inner body member in an assembled state. The inner body member 116 in the illustrated configuration comprises a base 120 and a substantially cylindrical inner shaft 122 extending from the base 120. The inner shaft 122 can include a resilient tab 124 (see FIGS. 8-10), the purpose of which is described below. The shielding member 118 in the illustrated configuration comprises a base, or base ring 126, a central opening 128 defined by the base ring 126 (see FIGS. 10, 11A-B), and a plurality of leg members 130 extending from the base ring 126.

Figure 6:
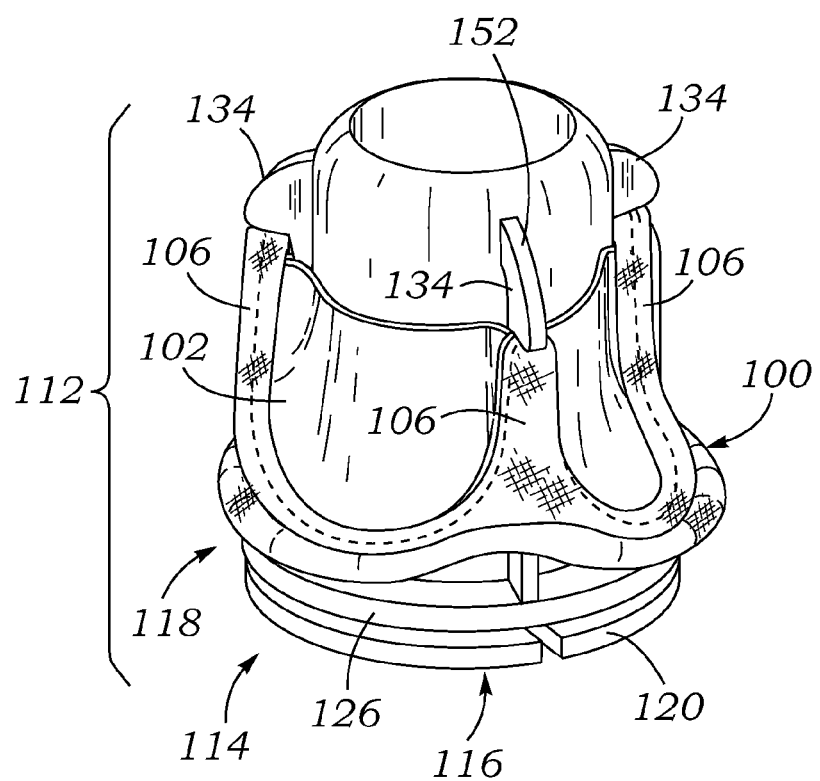
FIG. 6 is a perspective view of an exemplary assembled pre-shielded prosthetic heart valve assembly comprising a valve holder extending through the prosthetic heart valve and having a shielding member with distal end portions extending over and shielding the commissure tips.
Figure 11A:
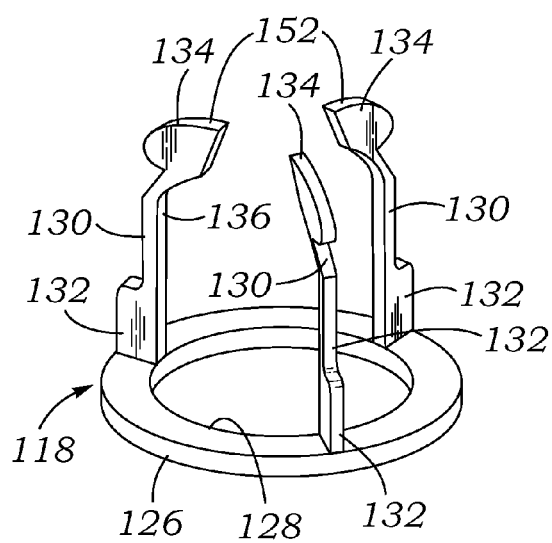
FIG. 11A is a perspective view of an exemplary shielding member with distal end portions in a relaxed, radially inward position.
Figure 11B:
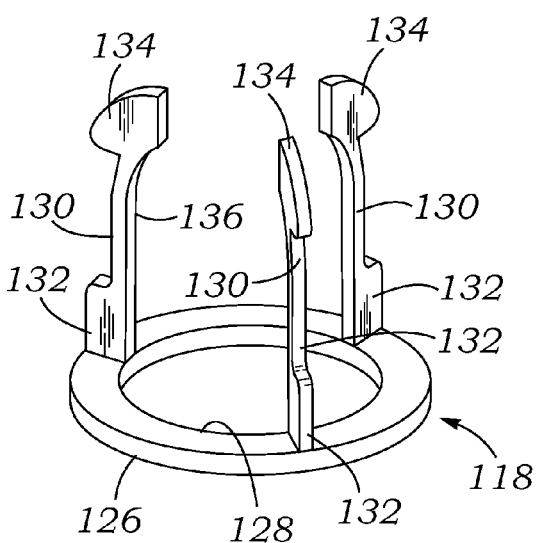
FIG. 11B is a perspective view of the exemplary shielding member of FIG. 11A with the distal end portions in a radially outward position.

As best shown in FIGS. 11A-11B, each leg member 130 has a respective proximal base portion 132 connected to the base ring 126, a respective distal end portion 134, and a respective intermediate portion 136 extending between the base portion and the distal end portion. The shielding member 118 desirably has the same number of leg members 130 as there are commissure posts 106 of the prosthetic valve. Thus, there are three such leg members 130 in the illustrated embodiment, although a greater or fewer number of leg members can be provided. The shaft 122 can be formed with a plurality of longitudinally extending, circumferentially spaced slots 138 configured to at least partially receive respective leg members 130 when the assembly is in the assembled state (as shown in FIG. 6). The leg members 130 desirably are spaced out substantially evenly around the base ring 126 to mirror the circumferential spacing of commissure posts 106 around the prosthetic valve 100.

The leg members 130 are normally biased to assume a radially inward position (FIG. 11A) and can flex or bend outwardly to a radially outward position (FIG. 11B). Thus, in the absence of any forces on the leg members 130, they assume the inward position shown in FIG. 11A; this can be referred to as the relaxed state of the leg members. However, when the shaft 122 of the inner body member 120 is inserted though the opening 128 of the base ring 128 and between the leg members 130, the leg members 130 are caused to deflect outwardly such that the distal end portions 134 are positioned to shield the commissure tips 108 (FIG. 6), as further described below. Conversely, removal of the shaft 122 from the space between the leg members 130 allows the leg members to flex or spring back to the radially inward position. In this manner, the leg members 130 can be referred to as cantilevered springs.

The distal end portions 134 can have a radial thickness that is greater than those of proximal and intermediate portions of the leg members 130. In particular embodiments, the distal end portions 134 comprise curved, convex distal end surfaces 152 facing away from the commissure tips 108 and are adapted to extent over and shield the commissure tips. The intermediate portions 136 of the leg members can be relatively thinner than the distal end portions 134 and the base portions 132 to facilitate deflection of the leg members between the deflected position (FIG. 11B) and non-deflected position (FIG. 11A).

To assemble the prosthetic valve 100 and the valve holder 114 in the manner shown in FIG. 6, the shielding member 118 is inserted through the prosthetic valve 100 (and the leaflets 102) until the distal end portions 134 extend beyond the commissure post tips 108 and the base ring 126 abuts or is adjacent the sewing ring 104 of the prosthetic valve. The inner shaft 122 of the inner body member 116 can then be inserted through the central opening 128 and between the leg members 130 such that the leg members 130 are aligned within respective slots 138 on the shaft 122. The shaft 122 is pushed through the leg members 130 to force the leg members and their distal end portions 134 into a radially outward position such that the distal end portions 134 extend over and shield the tips 108 of the commissure posts 106. As shown in FIGS. 8-10, the outer surface of the inner shaft 122 can have a resilient tab 124 projecting radially outwardly from the outer surface of the shaft. The tab 124 is shaped to allow the tab 124 to pass underneath the base ring 126 when the shaft 122 is inserted into the shielding member 118 yet engage the base ring 126 and prevent separation of the shaft 122 and shielding member 118 when the shaft is moved in the opposite direction. Thus, as the shaft 122 is inserted through the base ring 126 and between the leg members 130, the base ring 126 can contact the titled or canted outermost surface of the tab 124, which forces the tab to flex inwardly and allow the shaft 122 to be fully inserted between the leg members 130 (FIG. 6). When the tab 124 passes the base ring 126, the tab 124 flexes or springs back radially outwardly to its relaxed state.

FIG. 7 is a side perspective view of the prosthetic heart valve assembly 100 in an assembled state, showing placement of sutures 140 that secure the base 120 of the inner body member 116 to the base ring 126 of the shielding member 118. As shown, the proximal (inflow) surface 146 of the base 120 can include a plurality of radially extending slots 142. Each of the sutures 140 bridges across a respective slot and has two end portions that extend in the outflow direction through the base 120 and the base ring 126. The ends of each suture 140 passing through the base ring 126 can be tied together as shown at 144 so as to temporarily secure the inner body member 116 to the shielding member 118. The base 120 of the inner body member and the base ring 126 can have suture holes to allow the sutures 140 to pass through those components during assembly. The distal end portions 134 of the leg members 130 can engage the commissure tips 108 such that the prosthetic valve 100 is retained in place around the shielding member 118. In alternative embodiments, the same or additional sutures may secure the base 120 and/or the base ring 126 to the inflow end of the prosthetic valve 100 by, for example, threading the sutures through the sewing ring 104 of the prosthetic valve 100. The prosthetic valve 100 can be introduced into a patient's body and delivered to the desired implantation location (adjacent the mitral valve) in the assembled state shown in FIGS. 6 and 7. In the assembled state, the commissure posts 106 of the prosthetic valve 100 need not be bent or deflected inwardly and instead can be in a non-deflected, functional position for delivery into the body, as shown.

The proximal surface 146 of the base 120 of the inner body member 116 can include a centrally located threaded bore or opening that can receive the distal end portion of a shaft 148 of a delivery tool for manual delivery of the prosthetic heart valve assembly 100. The proximal end of the shaft 148 can be connected to a suitable handle for manipulation by a user. In other embodiments, the inner body member 116 may have other attaching mechanisms for connecting the shaft of a delivery tool. The present invention is not limited with respect to the type of delivery tool, handle or related apparatus or with respect to the type of connection to the delivery tool. Once the user has attached the delivery tool, the prosthetic heart valve assembly 100 may be delivered and secured to a native valve annulus in the heart such as the mitral valve annulus.

FIG. 6 shows the prosthetic valve 100 and the holder 114 as they are provided by the manufacturer in a sterile shipping container or package. The shaft of a delivery tool can be pre-attached to the holder 114 and packaged together with the prosthetic valve and the holder. In other embodiments, the delivery tool shaft can be packaged separately and can be mounted to the valve holder by a user just prior to a procedure. As noted above, the prosthetic valve 100 can have "dry" tissue leaflets and can be stored with the valve holder without a preserving solution. As such, any distortion of the leaflets 102 caused by the valve holder during storage does not permanently deform the leaflets, which can assume their normal functional shape once removed from the valve holder.

Although less convenient for a user, it should be noted that the prosthetic valve 100 and the valve holder 114 can be packaged in separate sterile containers or packages, in which case a user can mount the prosthetic valve to the valve holder in the manner described above just prior to a procedure. For example, the valve holder 114 can also be used to implant a prosthetic valve that is stored in a preserving solution. To avoid permanent leaflet deformation caused by the cross-linking process, it may be desirable to package the valve holder 114 separate from a prosthetic valve stored in a preserving solution.

To deliver and secure the prosthetic valve 100 to a native valve annulus, the user can secure an array of sutures to the native valve annulus, thread the sutures through the sewing ring 104 of the prosthetic valve 100, and slide the prosthetic valve assembly 100 along the sutures until the prosthetic valve 100 sits against the native valve annulus, as known in the art. As noted above, suture looping can occur when one or more of the sutures in the parachute array inadvertently wraps around the inside of one or more of the commissure post tips. The distal end portions 134 extend over the commissure post tips to protect against suture looping. The curved distal end surfaces 152 can contact and push the sutures away from the commissure post tips as the prosthetic valve is parachuted along the suture array.

FIGS. 8-9 show the process of disassembling the prosthetic heart valve assembly 100 and retracting the valve holder 114 from the prosthetic valve 100 once the prosthetic valve has been safely secured to a native valve annulus. First, the base 120 is mechanically disengaged from the base ring 126 and, if applicable, the prosthetic heart valve 100 by, for example, clipping the sutures 140 shown in FIG. 7. Next, as shown in FIG. 8, the inner body member 116, which may be connected to the shaft 148 of a delivery tool, is retracted away from the prosthetic valve 100 in the proximal direction as indicated by arrow 150. Retraction of the inner shaft 122 during this phase removes the outward radial force on the leg members 130 such that the distal end portions 134 flex inwardly of the commissure posts 106, thereby exposing the commissure tips 108. At this point or upon further withdrawal of the inner shaft 122, the tab 124 comes into contact with and engages the base ring 126. From this point onwards, as the inner body member 116 is further retracted in the proximal direction, the tab 124 causes the shielding member 118 to be retracted along with the inner body member 116 away from the prosthetic valve 100. With the distal end portions 134 in their relaxed, radially inward states, the shielding member 118 can be retracted through the leaflets 102 and completely removed from the prosthetic valve 100 along with the inner body member 116, as shown in FIG. 9.

Figure 12:
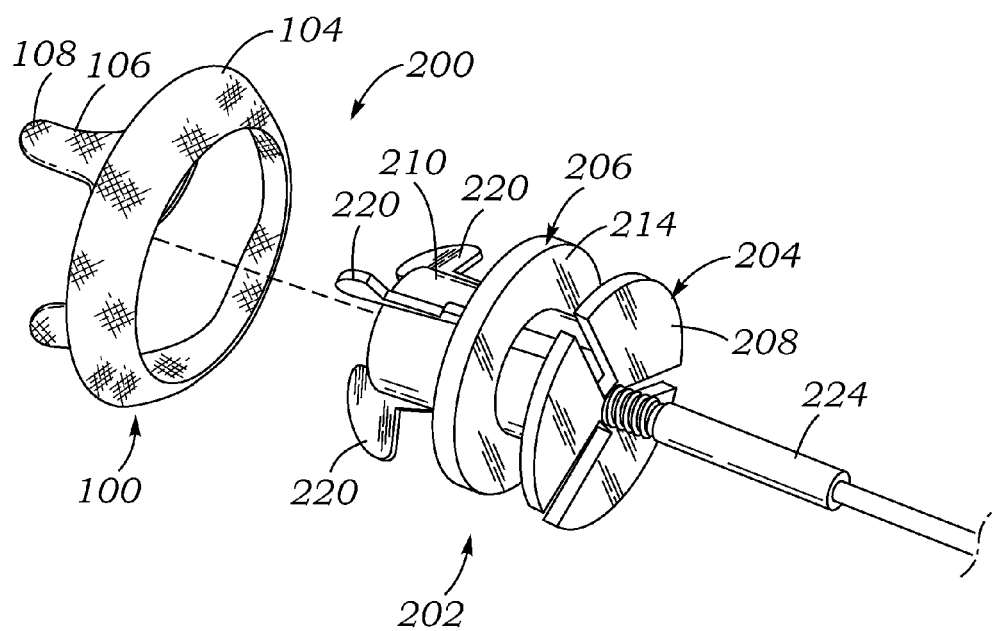
FIG. 12 is a side perspective view of an alternative embodiment of a pre-shielded prosthetic heart valve assembly in a dis-assembled state.

Although the inner shaft 122 is cylindrical and the central opening 128 is circular in the illustrated embodiment, the inner shaft and the central opening can have other shapes. For example, the inner shaft 122 can have a non-circular cross-sectional profile (in a plane perpendicular to its length) and the central opening 128 can be a non-circular shape, which can be the same or different shape than the cross-sectional profile of the inner shaft. Also, the inner shaft 122 can have a cross-sectional profile that varies along its length, such as a tapered inner shaft 210 (FIGS. 12-13, described below). In particular embodiments, the distal end portions 134 of the leg members can contact the commissure post tips 108, although in alternative embodiments the leg members can be configured such that there can be a small gap between the commissure post tips 108 and the distal end portions 134.

The inner body member 116 and the shielding member 118 can be made of any of various suitable materials, including metals or metal alloys (e.g., titanium, stainless steel, Nitinol, cobalt chromium alloys) or any of various polymeric materials, such as various polyamides, polyesters, or copolyesters. Some examples of polymers that can be used to form the inner body member 116 and/or the shielding member 118 include, without limitation, polyethylene terephthalate (PET), polytetrafluoroethylene (PTFE), or polyoxymethylene (POM). In a working embodiment, the shielding member 118 is made of titanium and the inner body member 116 is made of a suitable polymer.

In alternative embodiments, different techniques and/or mechanisms can be used to flex or move the leg members 130 between the inward and outward positions. For example, instead of an inner shaft 122, one or more levers or linkages can be operatively coupled to each of the leg members 130 to effect movement of the leg members between the inward and outward positions. The handle of the delivery tool can include a switch or actuator that is operably coupled to the leg members via the one or more levers or linkages such that activating the switch or actuator is effective to move the leg members 130.

FIG. 12 shows an alternative embodiment of a prosthetic heart valve assembly 200 in a partially disassembled state comprising a prosthetic heart valve 100 and a valve holder 202. FIG. 13 shows the valve holder 202 apart from the prosthetic valve 100. As shown in FIGS. 12 and 13, the valve holder 202 in the illustrated embodiment comprises an inner body member 204 and an outer shielding member 206. The inner body member 204 can comprise a base 208 and an inner shaft 210 projecting from the base 208. The inner shaft 210 can be tapered in a direction from the distal end of the shaft toward the base 208 such that a distal portion 212 of the shaft has a greater diameter than a proximal portion of the shaft adjacent the base 208. The base 208 can be connected to the distal end portion of a shaft 224 of a delivery tool. The shielding member 206 can comprises a base ring 214 defining a central opening 216 and a plurality of leg members 218 connected to and extending from the base ring 214. The leg members 218 can have wedge-shaped distal end portions 220 configured to extend over and shield the commissure post tips 108 during delivery of the prosthetic valve 100, as described above in connection with the embodiment of FIGS. 6-11.

In order to place the shielding member 206 around the tapered shaft 210 of the inner body member 204, the base ring 214 can be formed with a slit or gap 222. In this manner, the base ring 214 has a split-ring configuration that allows the base ring 214 to be splayed open and placed around the inner shaft 210, as depicted in FIG. 13. In particular embodiments, the inner diameter of the ring 214 is slightly larger than outer diameter of the proximal end portion of the inner shaft 210 adjacent the base 208. In alternative embodiments, the base ring 214 need not have a split ring configuration and instead the inner body member and the shielding member can be molded, machined or otherwise formed in an assembled state with the shielding member pre-positioned around the shaft 210.

To assemble the prosthetic valve 100 and the valve holder 202, the shaft 210 is held in a partially retracted position relative to the shielding member 206 to allow the distal end portions 220 to remain in a non-deflected state (as depicted in FIGS. 12 and 13). With the shielding member and the inner body member in this position, the leg members 218 can be inserted through the prosthetic valve 100 (and the leaflets 102) until the distal end portions 220 are distal to the commissure post tips 108. Once the base ring 214 abuts the inflow end of the prosthetic valve 100, the distal end portions 220 will be distal to, but still spaced radially inward of, the commissure post tips 108. The inner shaft 210 can then be advanced toward distal end portions 220, causing the leg members 218 to flex radially outwardly to position the distal end portions 220 over the commissure post tips 108. The distal end portion 212 of the tapered inner shaft 210 can be curved or rounded as in FIGS. 6-10 to assist in pushing the leg members 220 to the radially outward position as the shaft 210 is advanced through the shielding member. Once assembled, the valve holder 202 and the prosthetic valve 100 can be packaged together in a sterile container or package (with or without the shaft 224).

To disengage the valve holder 202 from the prosthetic heart valve 100 after the prosthetic valve has been sutured to a native valve annulus, sutures connecting the base 208 to the base ring 214 (not shown) are severed to disengage the inner body member 204 from the shielding member 206. The inner body member 204 is then retracted using a delivery tool. As the inner shaft 210 is withdrawn, the force from the distal portion of the inner shaft 210 pushing against the leg members 218 is removed. The distal end portions 220 are then able to retract to a radially inward position, thereby exposing the commissure post tips 108. As the shaft 210 is further withdrawn, the outer surface of the shaft 210 comes into contact with the base ring 214 at a location along the shaft where the outer diameter of the shaft 210 approximates the inner diameter of the central opening 216 of the base ring 214. In this manner, further retraction of the shaft 210 is effective to retract the shielding member 206 back through and away from the prosthetic valve.

FIG. 14 shows an alternative embodiment of a prosthetic valve assembly 300 comprising a prosthetic heart valve 100 and a valve holder 302. The valve holder 302 in the illustrated embodiment comprises a base 304, an inner shaft 306 extending from the base 304, and a deliver tool shaft 308 connected to the opposite side of the base from the inner shaft 306. The valve holder 302 can further include a plurality of distal shielding portions 310 spaced around the inner shaft 306. The distal shielding portions 310 can, in a first state, be at least partially housed within respective radially extending slots (not shown) formed in the inner shaft 324 and, in a second state, can project radially outward from the slots.

More specifically, during assembly of the prosthetic valve 100 and the valve holder 302, the distal shielding portions 310 may be retained inside the respective slots and/or the interior of the shaft such that the shielding portions 310 are spaced radially inwardly of the commissure post tips 108. In this position, the inner shaft 306 and the shielding portions 310 can be advanced through the prosthetic valve 100 (and the leaflets 102) toward the outflow end of the prosthetic valve. When the shielding portions 310 are advanced beyond the commissure post tips, the shielding portions 310 can be caused to project radially outwardly from the slots to extend over and shield the commissure post tips, as depicted in FIG. 14. Various techniques and/or mechanisms can be employed to cause the shielding portions 310 to project outwardly from the slots. In one particular embodiment, for example, the shielding portions 310 can be spring loaded and/or can be operatively connected to an actuator or switch on the handle by a linkage assembly or lever extending through the shaft 308. Actuating the actuator or switch causes the shielding members 310 to project outwardly from the inner shaft 310 to the position shown in FIG. 14.

The prosthetic valve 100 can be delivered and sutured to a native valve annulus in the heart using the valve holder 302 in the manner described above by sliding or parachuting the prosthetic valve 100 along an array of sutures secured to the native annulus. FIG. 14 shows a suture 314 contacting the distal end of one of the shielding portions 310. As the prosthetic valve is advanced toward the native annulus, the shielding portion 310 pushes or guides the suture 314 away from the commissure post 106 to prevent the suture from looping around the adjacent commissure post tip 108. Once the prosthetic valve 100 is secured to the native valve annulus, the switch/actuator on the handle of the delivery tool may be activated to retract the shielding portions 310 radially inwardly into the slots and/or the interior of the inner shaft 306 so that the shielding portions are spaced radially inwardly of the commissure post tips, after which the valve holder may be retracted through the prosthetic valve 100 and withdrawn from the body.

In particular embodiments, holders of the present invention include members configured to shield and/or constrict the commissure posts radially inward without necessarily using sutures in tension. Sutures in tension have been used in the past to constrict the commissure posts at the time of surgery, but may be unsuitable for long-term storage due to their tendency to creep over time. If sutures were used and they creeped and stretched while stored, the commissure posts could eventually flex outward, thus defeating the intended purpose. In terms of time frame, all previous mechanisms for shielding or constricting the valve commissure posts are designed to be actuated after removal from the sterile packaging and at the time of surgery. As a matter of good surgical practices, once a surgical implant has been removed from sterile packaging it should be implanted relatively soon or discarded to protect against contamination. Thus, for the purpose of definition, embodiments described herein in which the prosthetic valves and holder assemblies are pre-assembled with the commissure posts constricted and/or shielded by portions of the holder and then stored for later use refers to storage over a duration of at least 24 hours, to exclude those previous mechanisms designed to be actuated at the time of surgery.

While the invention has been described in its preferred embodiments, it is to be understood that the words which have been used are words of description and not of limitation. Therefore, changes may be made within the appended claims without departing from the true scope of the invention.

We claim:

1. A prosthetic heart valve assembly, comprising:
   a prosthetic heart valve having an inflow end with a peripheral sewing ring, an outflow end, three commissure posts ending in tips projecting in an outflow direction, and three flexible leaflets supported by the commissure posts that coapt against one another to provide one-way occluding surfaces; and
   a valve holder comprising:
      a commissure post shielding member having a proximal base ring and three circumferentially spaced leg members extending distally therefrom, each leg member having a length sufficient to extend at least partially through the flexible leaflets of the prosthetic valve in the outflow direction with the base ring positioned against the heart valve sewing ring, each leg member having a distal end portion and being moveable between a radially outward position and a radially inward position, wherein when the leg members are in the radially outward positions the distal end portions extend over and shield the tips of the commissure posts so as to extend over and shield the tips of the commissure posts from suture looping during advancement of the heart valve to a site of implantation, and wherein when the leg members are in the radially inward position the distal end portions are spaced radially inward of the commissure tips and can be withdrawn through the prosthetic valve in a direction toward the inflow end, the leg members being biased toward the radially inward position; and an inner shaft configured to extend through the base ring of the shielding member and between the leg members, the shaft having a shape that contacts the leg members and flexes the distal end portions outward to the radially outward positions, and wherein removal of the shaft in an inflow direction from within the leg members allows the leg members to spring back to the radially inward position, the shaft having a proximal end defining an opening for receiving a delivery tool for manual delivery of the prosthetic heart valve assembly.

2. The assembly of claim 1, wherein the distal end portion of each leg member has a radial thickness that is greater than a proximal portion of the leg member that extends through the prosthetic valve.

3. The assembly of claim 1, wherein the distal end portion of each leg member comprises a curved, convex distal end surface that faces away from the respective commissure tip that it covers.

4. The assembly of claim 1, wherein the flexible leaflets are bioprosthetic and the assembly is contained in a sterile package in a dry state.

5. The assembly of claim 1, wherein the shaft comprises a radially projecting tab configured to engage the base ring of the shielding member, the tab configured to permit the shaft to be inserted distally through the base ring of the shielding member to move the leg members to the radially outward positions while preventing the shaft from being removed proximally from within the base ring to enable removal of the shielding member with the shaft.

6. The assembly of claim 1, wherein the shaft extends distally from a proximal base portion that abuts the base ring of the shielding member and is releasably connected thereto.

7. The assembly of claim 6, wherein the base portion and base ring are sutured to the inflow end of the prosthetic valve.

8. The assembly of claim 1, wherein when the distal end portions are in their radially outward positions the commissure posts are in non-deflected, functional positions.

9. The assembly of claim 1, wherein the shaft includes a plurality of longitudinally extending, circumferentially spaced slots configured to at least partially receive respective leg members when the leg members flex to their radially inward positions.

10. The assembly of claim 1, wherein the shaft is tapered such that a distal portion has a greater diameter than a proximal portion.

11. A prosthetic heart valve assembly, comprising:
a prosthetic heart valve having an inflow end with a peripheral sewing ring, an outflow end, three commissure posts ending in tips projecting in an outflow direction, and three flexible leaflets supported by the commissure posts that coapt against one another to provide one-way occluding surfaces; and
a valve holder comprising:

a commissure post shielding member having a proximal base ring and three circumferentially spaced leg members extending distally therefrom, each leg member having a length sufficient to extend at least partially through the flexible leaflets of the prosthetic valve in the outflow direction with the base ring positioned against the heart valve sewing ring, each leg member having a distal end portion and being moveable between a radially outward position and a radially inward position, wherein when the leg members are in the radially outward positions the distal end portions extend over and shield the tips of the commissure posts so as to extend over and shield the tips of the commissure posts from suture looping during advancement of the heart valve to a site of implantation, and wherein when the leg members are in the radially inward position the distal end portions are spaced radially inward of the commissure tips and can be withdrawn through the prosthetic valve in a direction toward the inflow end, the leg members being biased toward the radially inward position; and an inner member configured to extend through the base ring of the shielding member and displace the distal end portions of the leg members outward to the radially outward positions, and wherein removal of the inner member in an inflow direction from within the leg members allows the leg members to spring back to the radially inward position, wherein the inner member has a radially projecting tab configured for one-way engagement of the inner member with the shielding member, the tab configured to permit the inner member to be inserted distally through the base ring of the shielding member to move the leg members to the radially outward positions while preventing the inner member from being removed proximally from within the base ring to enable removal of the shielding member along with the inner member.

12. The assembly of claim 11, wherein the distal end portion of each leg member has a radial thickness that is greater than a proximal portion of the leg member that extends through the prosthetic valve.

13. The assembly of claim 11, wherein the distal end portion of each leg member comprises a curved, convex distal end surface that faces away from the respective commissure tip that it covers.

14. The assembly of claim 11, wherein the flexible leaflets are bioprosthetic and the assembly is contained in a sterile package in a dry state.

15. The assembly of claim 11, wherein the inner member extends distally from a proximal base portion that abuts the base ring of the shielding member and is releasably connected thereto.

16. The assembly of claim 15, wherein the base portion and base ring are sutured to the inflow end of the prosthetic valve.

17. The assembly of claim 11, wherein when the distal end portions are in their radially outward positions the commissure posts are in non-deflected, functional positions.

18. The assembly of claim 11, wherein the inner member comprises a shaft with a plurality of longitudinally extending, circumferentially spaced slots configured to at least partially receive respective leg members when the leg members flex to their radially inward positions.

19. The assembly of claim 18, wherein the shaft is tapered such that a distal portion has a greater diameter than a proximal portion.

\* \* \* \* \*